(12) United States Patent
Metsack et al.

(10) Patent No.: US 11,701,477 B2
(45) Date of Patent: Jul. 18, 2023

(54) HEATING AND COOLING SYSTEM FOR INTRAVENOUS FLUIDS

(71) Applicant: Western New England University, Springfield, MA (US)

(72) Inventors: Austen P. Metsack, Ashford, CT (US); Joseph W. Wetzel, Oakdale, NY (US); Jingru Z. Benner, Springfield, MA (US)

(73) Assignee: WESTERN NEW ENGLAND UNIVERSITY, Springfield, MA (US)

( * ) Notice: Subject to any disclaimer, the term of this patent is extended or adjusted under 35 U.S.C. 154(b) by 516 days.

(21) Appl. No.: 16/986,392

(22) Filed: Aug. 6, 2020

(65) Prior Publication Data
US 2021/0038832 A1    Feb. 11, 2021

Related U.S. Application Data

(60) Provisional application No. 62/883,315, filed on Aug. 6, 2019.

(51) Int. Cl.
*A61M 5/44* (2006.01)

(52) U.S. Cl.
CPC ..... *A61M 5/445* (2013.01); *A61M 2205/3368* (2013.01); *A61M 2205/366* (2013.01); *A61M 2205/3606* (2013.01)

(58) Field of Classification Search
CPC .. A61M 2205/3368; A61M 2205/3372; A61M 2205/36; A61M 2205/3606; A61M 2205/3626; A61M 2205/366; A61M 2205/3673; A61M 5/445
See application file for complete search history.

(56) References Cited

U.S. PATENT DOCUMENTS

| 4,210,153 | A | * | 7/1980 | Fehlau | ............ | A61B 5/441 |
| | | | | | | 600/369 |
| 5,108,372 | A | | 4/1992 | Swenson | | |
| 5,729,653 | A | * | 3/1998 | Magliochetti | ........ | A61M 5/44 |
| | | | | | | 392/491 |
| 6,376,805 | B2 | | 4/2002 | Faries, Jr. et al. | | |
| 6,660,974 | B2 | * | 12/2003 | Faries, Jr. | ........ | A61F 7/0241 |
| | | | | | | 219/400 |
| 6,743,201 | B1 | * | 6/2004 | Donig | ........... | A61M 1/166 |
| | | | | | | 165/169 |
| 6,830,581 | B2 | | 12/2004 | Magers | | |

(Continued)

*Primary Examiner* — Quynh-Nhu H. Vu
(74) *Attorney, Agent, or Firm* — Cantor Colburn LLP

(57) ABSTRACT

An intravenous fluid conditioning system includes a housing having a first chamber and a second chamber. A volume of heat transfer medium is located in the first chamber and the second chamber. A first intravenous fluid line extends through the first chamber and a second intravenous fluid line extends through the second chamber. One or more thermoelectric devices are located in the housing, such that a first side of each of the one or more thermoelectric devices is in thermal communication with the first chamber and a second side of each of the one or more thermoelectric devices opposite the first side is in thermal communication with the second chamber. The one or more thermoelectric devices exchange thermal energy with a volume of intravenous fluid selectably flowed through the first intravenous fluid line or the second intravenous fluid line to condition the intravenous fluid.

13 Claims, 4 Drawing Sheets

(56) References Cited

U.S. PATENT DOCUMENTS

| | | |
|---|---|---|
| 6,974,463 B2 | 12/2005 | Magers et al. |
| 7,896,834 B2 | 3/2011 | Smisson, III et al. |
| 9,285,137 B2* | 3/2016 | Peters ................. A61M 1/1662 |
| 9,642,974 B2* | 5/2017 | King ....................... A61M 5/44 |
| 2003/0187380 A1* | 10/2003 | Botto ................... B01D 61/425 |
| | | 604/6.08 |

* cited by examiner

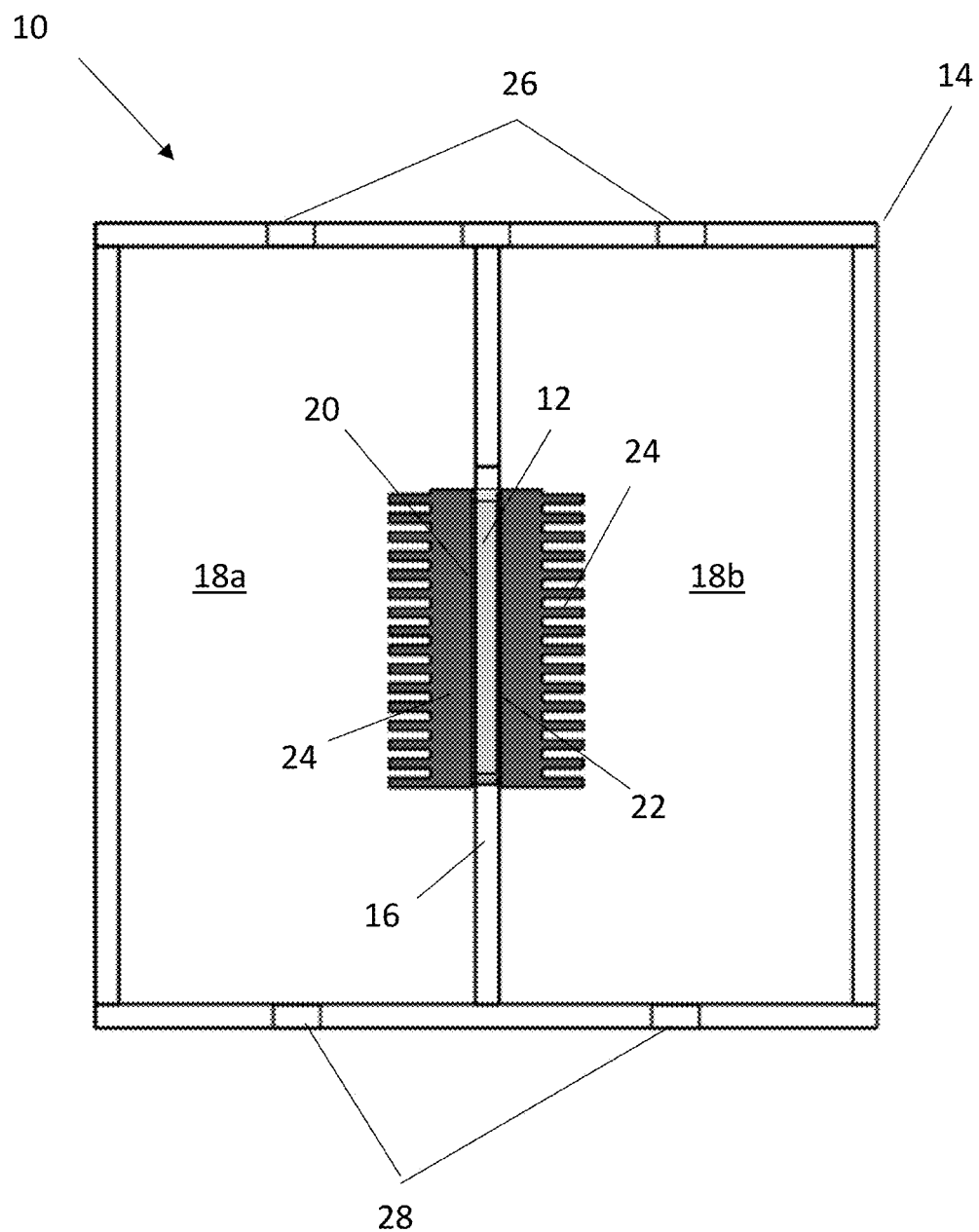

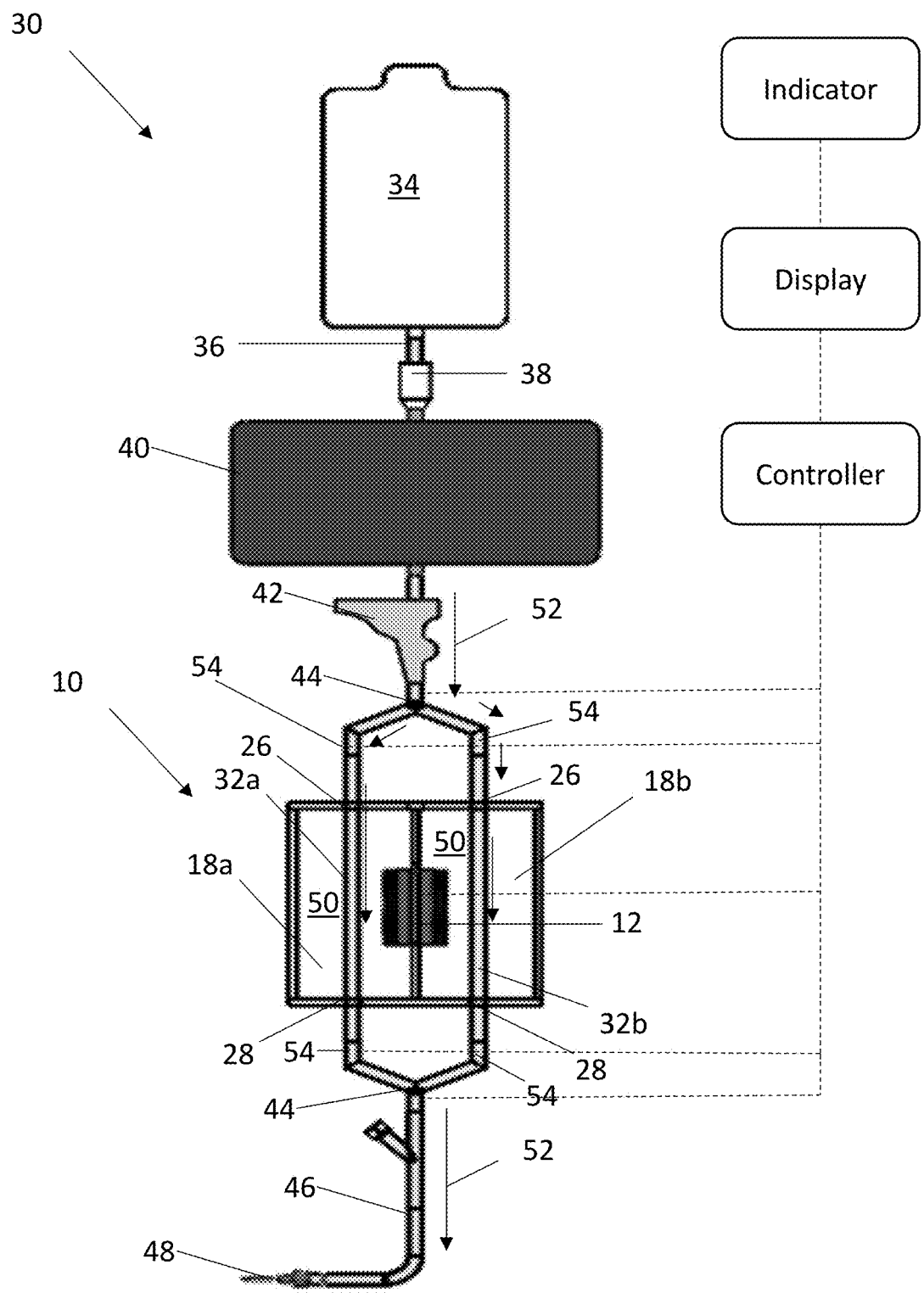

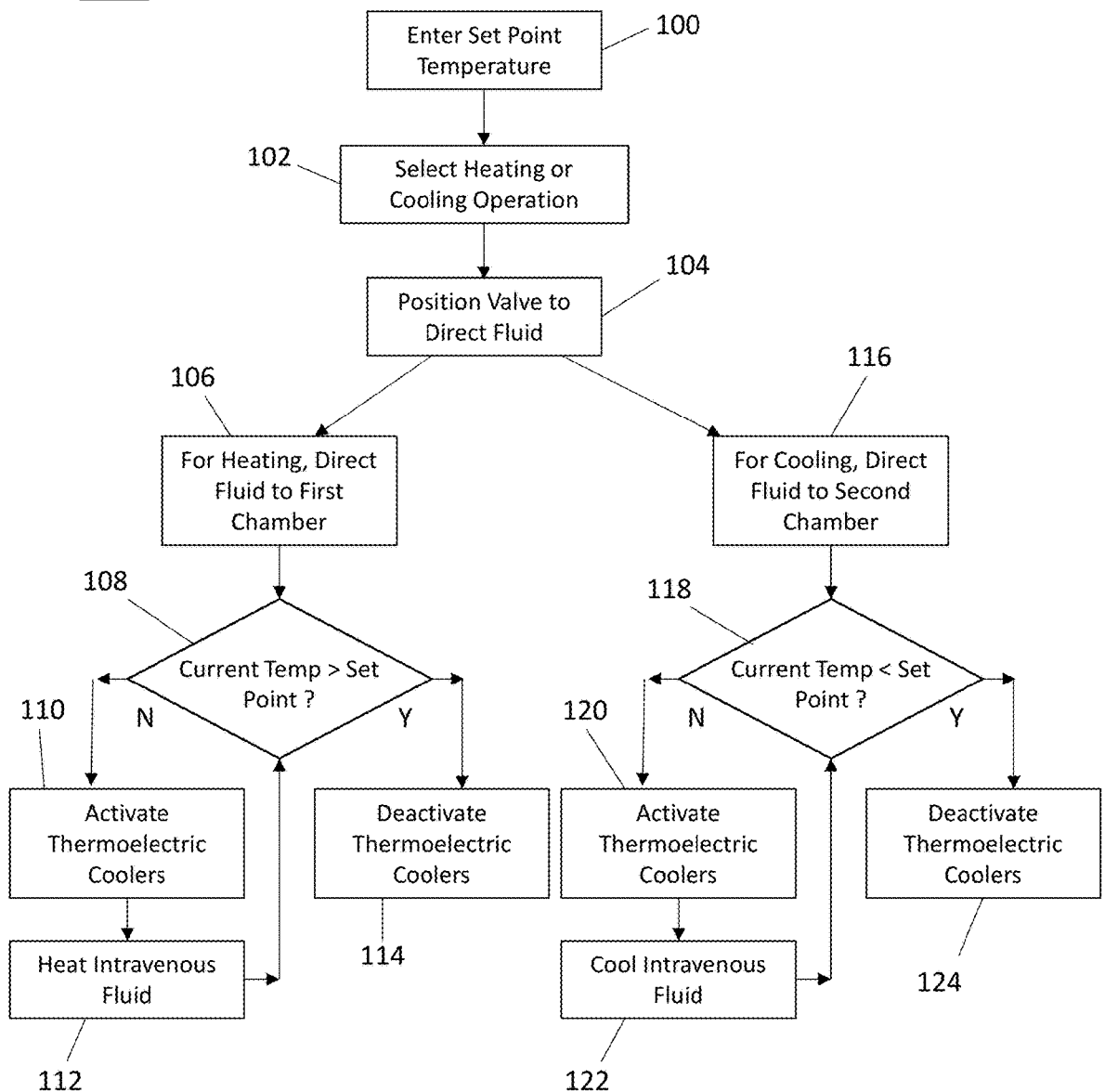

HEATING AND COOLING SYSTEM FOR INTRAVENOUS FLUIDS

CROSS-REFERENCE TO RELATED APPLICATIONS

This application claims the benefit of U.S. Provisional Application No. 62/883,315 filed Aug. 6, 2019, the disclosure of which is incorporated herein by reference in its entirety.

BACKGROUND

Exemplary embodiments pertain to the art of medical technology, and more particularly to the supply of intravenous fluids to a patient.

Intravenous fluid bags are typically stored at room temperature, or at about 70 degrees Fahrenheit. Introducing 70 degree Fahrenheit fluid into a patient's body having an internal temperature of 98 degrees Fahrenheit causes patient discomfort and stress. Studies show that patients shiver when receiving intravenous fluids because their body tries to remain at normal body temperatures. Currently, to warm bags, nurses and EMTs will rub the bags in blankets or other clothes in order to warm the fluid. However, this can be time-consuming and the fluid temperature is still unknown when such a process is complete. Similarly, EMTs and nurses use ice baths and evaporation (mist) to cool heat-stroke victims. These methods are restricted to location and resources and can be time-consuming to acquire the necessary materials.

BRIEF DESCRIPTION

In one embodiment, an intravenous fluid conditioning system includes a housing having a first chamber and a second chamber. A volume of heat transfer medium is located in the first chamber and the second chamber. A first intravenous fluid line extends through the first chamber and a second intravenous fluid line extends through the second chamber. One or more thermoelectric devices are located in the housing, such that a first side of each of the one or more thermoelectric devices is in thermal communication with the first chamber and a second side of each of the one or more thermoelectric devices opposite the first side is in thermal communication with the second chamber. The one or more thermoelectric devices exchange thermal energy with a volume of intravenous fluid selectably flowed through the first intravenous fluid line or the second intravenous fluid line to condition the intravenous fluid.

Additionally or alternatively, in this or other embodiments a valve is operably connected to the first intravenous fluid line and the second intravenous fluid line to selectably direct the volume of intravenous fluid through the first intravenous fluid line or the second intravenous fluid line.

Additionally or alternatively, in this or other embodiments one or more temperature sensors are operably connected to the first chamber and the second chamber to detect a temperature of the first chamber and/or the second chamber.

Additionally or alternatively, in this or other embodiments a display is configured to display a temperature of the first chamber and/or the second chamber and a set point temperature.

Additionally or alternatively, in this or other embodiments the volume of intravenous fluid is heated by flowing through the first chamber and cooled by flowing through the second chamber.

Additionally or alternatively, in this or other embodiments one or more heat sinks are operably connected to the first side and extending into the first chamber, and one or more heat sinks are operably connected to the second side and extending into the second chamber.

Additionally or alternatively, in this or other embodiments the one or more heat sinks are two heat sinks per chamber.

Additionally or alternatively, in this or other embodiments the heat transfer medium is one of water or glycol or other medium.

Additionally or alternatively, in this or other embodiments the housing is formed from a medical grade material.

Additionally or alternatively, in this or other embodiments one or more plugs in the housing allow for access to the first chamber and the second chamber.

Additionally or alternatively, in this or other embodiments the one or more thermoelectric devices are two thermoelectric devices.

Additionally or alternatively, in this or other embodiments a fluid pump is operably connected to the first intravenous fluid line and the second intravenous fluid line.

Additionally or alternatively, in this or other embodiments the fluid pump is disposed upstream of the housing.

In another embodiment, a method of conditioning an intravenous fluid includes determining a desired temperature of an intravenous fluid, comparing the desired temperature to an actual temperature of the intravenous fluid, and flowing the intravenous fluid through a housing, the housing containing a thermoelectric device. The thermoelectric device is activated, and thermal energy is exchanged between the intravenous fluid and the thermoelectric device, thereby conditioning the intravenous fluid.

Additionally or alternatively, in this or other embodiments the housing has a first chamber and a second chamber, and the thermoelectric device includes a first side in thermal communication with the first chamber and a second side opposite the first side in thermal communication with the second chamber, and the method includes selectably directing the intravenous fluid through the first chamber or the second chamber depending on whether the conditioning requires heating or cooling of the intravenous fluid.

Additionally or alternatively, in this or other embodiments a temperature of the first chamber and/or the second chamber is monitored via one or more temperature sensors.

Additionally or alternatively, in this or other embodiments thermal energy is exchanged between the intravenous fluid and the thermoelectric device via a thermal exchange medium disposed in the first chamber and the second chamber.

Additionally or alternatively, in this or other embodiments the intravenous fluid is selectably directed through the first chamber or the second chamber via operation of a valve.

Additionally or alternatively, in this or other embodiments the volume of intravenous fluid is heated by flowing through the first chamber and cooled by flowing through the second chamber.

Additionally or alternatively, in this or other embodiments the intravenous fluid is urged through the first chamber or the second chamber via an intravenous fluids pump or just by using a simple gravity fed operation.

BRIEF DESCRIPTION OF THE DRAWINGS

The following descriptions should not be considered limiting in any way. With reference to the accompanying drawings, like elements are numbered alike:

FIG. 2 is another schematic illustration of an embodiment of a conditioner for intravenous fluids;

FIG. 3 is a schematic illustration of an intravenous fluid conditioning system; and FIG. 4 is a schematic illustration of a method of operating a conditioning system for intravenous fluids.

DETAILED DESCRIPTION

Figure 1:
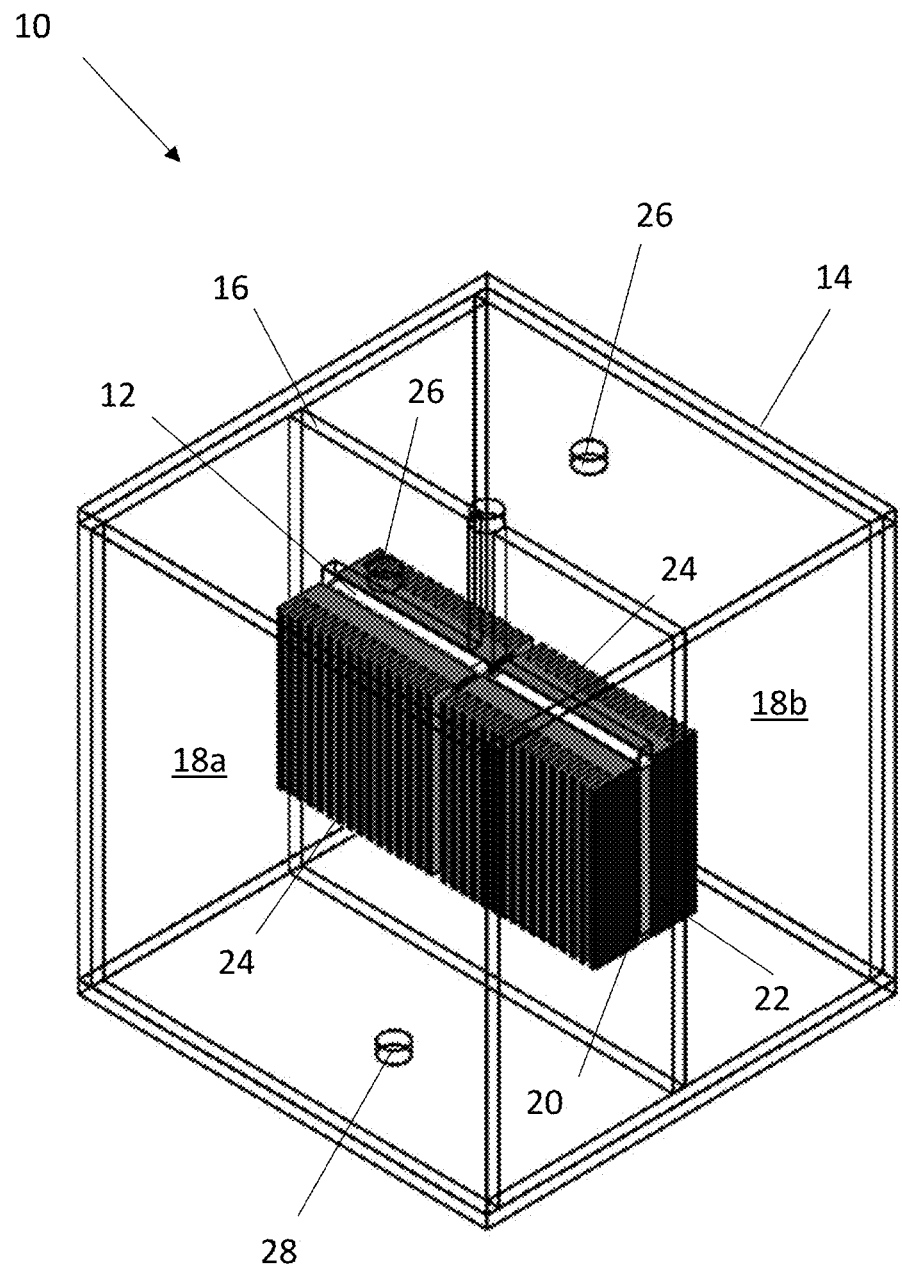
FIG. 1 is a schematic illustration of an embodiment of a conditioner for intravenous fluids.

A detailed description of one or more embodiments of the disclosed apparatus and method are presented herein by way of exemplification and not limitation with reference to the Figures.

Shown in FIGS. 1 and 2 is a schematic illustration of an embodiment of an intravenous fluid conditioner 10. The intravenous fluid conditioner 10 is configured to selectably heat or cool an intravenous fluid flow prior to the intravenous fluid flow. The conditioner 10 utilizes one or more heating and cooling devices positioned in a housing 14. The housing 14 is formed from, for example, a medical grade material. In some embodiments, the heating and cooling devices are thermoelectric devices 12 such as Peltier coolers, to cool and/or heat the intravenous fluid. In some embodiments, the housing 14 is formed from medical grade material, but it is to be appreciated that other materials may be utilized. While in some embodiments, Peltier devices are utilized, in other embodiments other mechanisms such as a heating film may be utilized. The housing 14 includes a divider 16 to define two chambers 18 in the housing 14. The thermoelectric devices 12 are located at the divider 16, each thermoelectric device 12 having a first side 20 or "heating side" facing a first chamber 18a and a second side 22 or "cooling side" facing a second chamber 18b. Each thermoelectric device 12 has a heat sink 24 extending from each of the first side 20 and the second side 22. While the embodiment in FIG. 1 includes two thermoelectric devices 12 and four heat sinks 24, it is to be appreciated that other embodiments may include other numerical combinations of thermoelectric devices 12 and heat sinks 24 may be utilized. The chambers 18a, 18b each include a chamber inlet 26 and a chamber outlet 28.

Referring now to FIG. 3, the conditioner 10 is part of an intravenous fluid delivery system 30. The first chamber 18a has a first intravenous fluid line 32a routed therethrough via the chamber inlet 26 and the chamber outlet 28 of the first chamber 18a. Similarly, the second chamber 18b has a second intravenous fluid line 32b routed therethrough via the chamber inlet 26 and the chamber outlet 28 of the second chamber 18b. Each of the chamber inlet 26 and chamber outlet 28 may include a gasket (not shown) or other seal mechanism to seal between the chamber inlet 26/chamber outlet 28 and the intravenous fluid line 32.

The intravenous fluid delivery system 30 includes an intravenous fluid source 34 such as a bag. An intravenous fluid source line 36 extends from the intravenous fluid source 34 toward the intravenous fluid conditioner 10. Other components, such as a drip chamber 38, a fluid pump 40 and a roller clamp 42 may be located along the intravenous source line 36 between the intravenous fluid source 34 and the intravenous fluid conditioner 10. Upstream of the housing 14, the intravenous fluid source line 36 is connected to the first intravenous fluid line 32a and the second intravenous fluid line 32b. In some embodiments, the connection may be via a valve 44, for example a three-way switching valve, which is configured to selectable direct intravenous fluid from the intravenous fluid source line 36 to the first intravenous fluid line 32a and/or the second intravenous fluid line 32b. Downstream of the intravenous fluid conditioner 10, the first intravenous fluid line 32a and the second intravenous fluid line 32b are joined via, for example, a second valve 44, to form an intravenous fluid outlet line 46, through which conditioned intravenous fluid is directed to a patient via, for example, a needle 48.

The chambers 18a, 18b are filled with a heat transfer medium 50, such as water, glycol or other fluid medium. In operation, the thermoelectric devices 12, via current flow therethrough, the heat sinks 24 and the heat transfer medium 50 facilitate the heating or cooling of the intravenous fluid 52 flowing through the intravenous fluid lines 32a, 32b. The system 10 is configured such that one chamber, for example, first chamber 18a, is configured as a heating chamber while another chamber, for example, second chamber 18b, is configured as a cooling chamber. Each chamber 18a, 18b may include a stirring device (not shown) located therein to circulate the heat transfer medium 50 located in the chambers 18a, 18b.

The valve 44 is operably connected to the intravenous fluid lines 32a, 32b to selectably direct the intravenous fluid 52 through the first chamber 18a and/or the second chamber 18b, depending on whether heating or cooling of the intravenous fluid 52 is desired to provide the intravenous fluid 52 at a selected temperature to the patient.

The thermoelectric devices 12 are supplied electrical current via electrical leads (not shown) extending through the housing 14 and operably connected to the thermoelectric devices 12. Depending on the level of temperature change of the intravenous fluid 52 desired, the thermoelectric devices 12 may be selectably turned on or turned off. For example, when the level of temperature change desired is relatively low, one thermoelectric device 12 may be operated, while when the when the level of temperature change desired is relatively high, two or more thermoelectric devices 12 may be operated. Temperature sensors 54, for example, thermistors, are located at the chambers 18a and 18b, for example at chamber inlets 26 and chamber outlets 28 to detect the temperature of the intravenous fluid 52 entering and/or exiting the chambers 18a, 18b. The intravenous fluid delivery system 30 may include a temperature display 56. The temperature display 56 is configured to display a fluid temperature and a desired or set point temperature. The temperature sensors 54 and the thermoelectric devices 12 are operably connected to a system controller 58 which monitors and drives operation of the system 30.

The system 30 may utilize the fluid pump 40 located upstream of the housing 14 and the valve 44 as shown in FIG. 3 to urge the intravenous fluid 52 through the housing 14. It is to be appreciated that in other embodiments the fluid pump 40 may be located downstream of the housing 14. In yet other embodiments the fluid pump 40 may be omitted, with flow of intravenous fluid 52 through the housing 14 accomplished via gravity. An indicator 60, such as an LED or other light, is connected to the system controller 58 and is configured to be illuminated when operation of the thermoelectric devices 12 is activated.

Referring now to FIG. 4, a method of operating the system 30 is illustrated. Initially, at block 100 a desired temperature or set point is entered into the system controller 58. At block 102, heating operation or cooling operation of the system 30 is selected and at block 104 the valve 44 is positioned to direct the intravenous fluid 52 through the first chamber 18a for heating operation or positioned to direct the intravenous fluid 52 through the second chamber 18b for cooling operation.

For heating operation, at block 106, the intravenous fluid 52 is directed along the intravenous fluid line 32a extending through the first chamber 18a. At block 108, the system controller 58 reads the current temperature via the temperature sensors 54, and compares the current temperature to the set point temperature. If the current temperature is not greater than the set point temperature, the indicator 60 is illuminated and the thermoelectric devices 12 are activated at block 110. The thermoelectric devices 12 exchange thermal energy with the intravenous fluid 52 via the heat sinks 24 and the heat transfer medium 50 in first chamber 18a to heat the intravenous fluid 52 at block 112. The current temperature is periodically compared to the set point temperature at block 108. If the current temperature is greater than the set point temperature, the indicator 60 and the thermoelectric devices 12 are turned off at block 114.

For cooling operation, at block 116 the intravenous fluid 52 is directed along the intravenous fluid line 32b extending through the second chamber 18b. At block 118, the system controller 58 reads the current temperature via the temperature sensors 54, and compares the current temperature to the set point temperature. If the current temperature is not less than the set point, the indicator 60 is illuminated and the thermoelectric devices 12 are activated at block 120. The thermoelectric devices 12 exchange thermal energy with the intravenous fluid 52 via the heat sinks 24 and the heat transfer medium 50 in second chamber 18b to cool the intravenous fluid 52 at block 122. The current temperature is periodically compared to the set point temperature at block 118 using a proportional differential integral control (PDIC).

The PDIC shuts the thermoelectric devices 12 off at block 124 before the temperature of the intravenous fluids 52 go above the set point temperature at block 100. The temperature will continue to rise after the thermoelectric devices 12 are shut off, but the PDIC takes this into account ensuring the fluids will never go above the temperature set point determined at block 100.

The system 10 disclosed herein has many advantages, including a unique ability to precisely heat or cool intravenous fluids at the command of the user. This ability to heat or cool the intravenous fluids precisely and quickly allows the system disclosed herein to be used by medical personnel for a wide array of different treatments and applications. Additionally, the present system allows for active monitoring of the current temperature relative to a set point or desired temperature and includes active control of the heating and cooling operation. The system interface allows the medical personnel using the device to input a temperature that the device will either cool or heat to while simultaneously giving an instantaneous temperature readout. These features coupled together allows for a much more precise operation leading to a much more effective treatment for the patient. Other devices include complex induction heating mechanisms and intricate circuits making it difficult for medical personnel to perform regular maintenance and repairs which can lead to the device being unusable for an extended period of time. Further, unlike traditional intravenous fluid warmers or devices that contain their own intravenous fluids pump, the system disclosed herein is a completely stand-alone device that can be adapted to work in conjunction with any intravenous fluids pump or just by using a simple gravity fed operation.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. An intravenous fluid conditioning system, comprising:
a housing having a first chamber and a second chamber;
a volume of heat transfer medium disposed in the first chamber and the second chamber;
a first intravenous fluid line extending through the first chamber;
a second intravenous fluid line extending through the second chamber; and
one or more thermoelectric devices disposed in the housing, such that a first side of each of the one or more thermoelectric devices is in thermal communication with the first chamber and a second side of each of the one or more thermoelectric devices opposite the first side is in thermal communication with the second chamber;
wherein the one or more thermoelectric devices exchange thermal energy with a volume of intravenous fluid selectably flowed through the first intravenous fluid line or the second intravenous fluid line to condition the intravenous fluid.

2. The intravenous fluid conditioning system of claim 1, further comprising a valve operably connected to the first intravenous fluid line and the second intravenous fluid line to selectably direct the volume of intravenous fluid through the first intravenous fluid line or the second intravenous fluid line.

3. The intravenous fluid conditioning system of claim 1, further comprising one or more temperature sensors operably connected to the first chamber and the second chamber to detect a temperature of the first chamber and/or the second chamber.

4. The system of claim 3, further comprising a display configured to display a temperature of the first chamber and/or the second chamber and a set point temperature.

5. The system of claim 1, wherein the volume of intravenous fluid is heated by flowing through the first chamber and cooled by flowing through the second chamber.

6. The system of claim 1, further comprising:
one or more heat sinks operably connected to the first side and extending into the first chamber; and
one or more heat sinks operably connected to the second side and extending into the second chamber.

7. The system of claim 6, wherein the one or more heat sinks are two heat sinks.

8. The system of claim 1, wherein the heat transfer medium is one of water or glycol.

9. The system of claim 1, wherein the housing is formed from one of a medical grade material.

10. The system of claim 1, further comprising one or more plugs in the housing to allow for access to the first chamber and the second chamber.

11. The system of claim 1, wherein the one or more thermoelectric devices are two thermoelectric devices.

12. The system of claim 1, further comprising a fluid pump operably connected to the first intravenous fluid line and the second intravenous fluid line.

13. The system of claim 12, wherein the fluid pump is disposed upstream of the housing.

* * * * *